(12) United States Patent
Mitsunaka et al.

(10) Patent No.: US 10,571,422 B2
(45) Date of Patent: Feb. 25, 2020

(54) SENSOR CIRCUIT

(71) Applicant: SHARP KABUSHIKI KAISHA, Sakai, Osaka (JP)

(72) Inventors: Takeshi Mitsunaka, Sakai (JP); Kunihiko Iizuka, Sakai (JP); Akira Saito, Sakai (JP); Nobuyuki Ashida, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 28 days.

(21) Appl. No.: 15/770,860

(22) PCT Filed: Sep. 21, 2016

(86) PCT No.: PCT/JP2016/077834
§ 371 (c)(1),
(2) Date: Apr. 25, 2018

(87) PCT Pub. No.: WO2017/077782
PCT Pub. Date: May 11, 2017

(65) Prior Publication Data
US 2018/0356360 A1    Dec. 13, 2018

(30) Foreign Application Priority Data

Nov. 5, 2015 (JP) ................................. 2015-217822

(51) Int. Cl.
*G01N 27/22* (2006.01)
(52) U.S. Cl.
CPC ......... *G01N 27/228* (2013.01); *G01N 27/221* (2013.01); *G01N 27/223* (2013.01); *G01N 27/226* (2013.01); *G01N 27/227* (2013.01)

(58) Field of Classification Search
CPC .. G01N 27/228; G01N 27/227; G01N 27/226; G01N 27/223; G01N 27/221
(Continued)

(56) References Cited

U.S. PATENT DOCUMENTS 5,986,549 A * 11/1999 Teodorescu .......... A61B 5/6892
324/207.16
2009/0267596 A1* 10/2009 Wang ................. G01R 33/1269
324/228

FOREIGN PATENT DOCUMENTS

JP    S59-095448 A    6/1984
JP    H04-076451 A    3/1992
(Continued)

OTHER PUBLICATIONS

C. Sideris, A. Hajimiri, "An Integrated magnetic Spectrometer for Multiplexed Biosensing", IEEE Solid-State Circuit Conf. Dig. Tech. papers, pp. 300-302, Feb. 2013.
(Continued)

*Primary Examiner* — Melissa J Koval
*Assistant Examiner* — Trung Nguyen
(74) *Attorney, Agent, or Firm* — ScienBiziP, P.C.

(57) ABSTRACT

To detect changes in the physical properties of an examination object as changes in a plurality of different oscillation frequencies using signals with the oscillation frequencies, a sensor circuit includes: an oscillation circuit (1) with a first resonant frequency; an oscillation circuit (2) with a second resonant frequency different from the first resonant frequency; and a detection circuit (4) that detects oscillation frequencies of the oscillation circuit (1) and the oscillation circuit (2).

5 Claims, 11 Drawing Sheets

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
M1-M4: TRANSISTORS
M5: SWITCH TRANSISTOR

(58) Field of Classification Search
USPC ....... 324/600, 668, 633, 636, 652, 675, 682,
324/708, 500, 529, 530
See application file for complete search history.

(56) References Cited

FOREIGN PATENT DOCUMENTS

| JP | H10-062390 A | 3/1998 |
|----|--------------|--------|
| JP | 2002-159523 A | 6/2002 |

OTHER PUBLICATIONS

H. Yada, M. Nagai, K. Tanaka, "Origin of the fast relaxation component of water and heavy water revealed by terahertz time-domain attenuated total reflection spectroscopy", Chemical Physics Letters, pp. 166-170, 2008.

\* cited by examiner

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
M1-M4: TRANSISTORS
M5: SWITCH TRANSISTOR

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
31: EXAMINATION OBJECT
M1-M4: TRANSISTORS
M5: SWITCH TRANSISTOR

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
32: EXAMINATION OBJECT
M1-M4: TRANSISTORS
M5: SWITCH TRANSISTOR

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
41: EXAMINATION OBJECT
M1-M4: TRANSISTORS
M5: SWITCH TRANSISTOR

1: OSCILLATION CIRCUIT
2: OSCILLATION CIRCUIT
3: FREQUENCY-DIVIDING CIRCUIT
4: DETECTION CIRCUIT
10: SENSOR CIRCUIT
11: RESONANCE CIRCUIT
12: INDUCTOR
13: CAPACITOR
14: CURRENT SOURCE
15: CAPACITOR
21: RESONANCE CIRCUIT
22: INDUCTOR
23: CAPACITOR
42: EXAMINATION OBJECT
M1-M4: TRANSISTORS
M5: SWITCH TRANSISTOR

1: OSCILLATION CIRCUIT
2: OSCILLATION CIRCUIT
3: FREQUENCY-DIVIDING CIRCUIT
4: DETECTION CIRCUIT
11: RESONANCE CIRCUIT
14: CURRENT SOURCE
15: CAPACITOR
21: RESONANCE CIRCUIT
50: SENSOR CIRCUIT
52: CAPACITOR
53: INDUCTOR
62: CAPACITOR
63: INDUCTOR
M1-M4: TRANSISTORS
M5: SWITCH TRANSISTOR

| | |
|---|---|
| 101: SEMICONDUCTOR SUBSTRATE | 114: EXAMINATION OBJECT |
| 110: OSCILLATOR | 120: OSCILLATOR |
| 111: INDUCTOR | 121: INDUCTOR |
| 112: ANOTHER CIRCUIT | 122: ANOTHER CIRCUIT |
| 113: MAGNETIC PARTICLES | 124: EXAMINATION OBJECT |

US 10,571,422 B2

SENSOR CIRCUIT

TECHNICAL FIELD

The present invention relates to a sensor circuit that includes a radio-frequency (RF) oscillator and that detects a change in an examination object including moisture.

BACKGROUND ART

Low cost, miniaturization, shortening of examination time, simplicity of operation, and so forth are required for human diagnostic equipment used in each household, simple diagnostic facility, and the like. A sensor IC (Integrated Circuit) formed on a semiconductor integrated circuit can satisfy these requirements.

For example, PTL 1 discloses an example of a sensor IC formed on a semiconductor integrated circuit. The sensor IC according to PTL 1 will be described with reference to FIGS. 9 to 11.

Part (a) of FIG. 9 is a schematic diagram illustrating the configuration of the sensor IC of PTL 1, and part (b) of FIG. 9 is a circuit diagram of the sensor IC of PTL 1.

As illustrated in part (a) of FIG. 9, the sensor IC of PTL 1 has a configuration where oscillators 110 and 120 are arranged in parallel on a semiconductor substrate 101. The oscillator 110 includes an inductor 111 and another circuit 112, and the oscillator 120 includes an inductor 121 and another circuit 122. The inductors 111 and 121 are formed of metal layers on the semiconductor substrate 101. As illustrated in part (b) of FIG. 9, the other circuits 121 and 122 include transistors and capacitors.

Part (a) of FIG. 10 is a schematic diagram illustrating a state in which magnetic particles and an examination object are brought into contact with one inductor of the sensor IC, and part (b) of FIG. 10 is a diagram illustrating a state in which a further examination object is brought into contact with the other conductor.

As illustrated in part. (a) of FIG. 10, when an examination object 114 is brought into contact with the semiconductor substrate 101 illustrated in part (a) of FIG. 9, the permeability changes as a result of fluctuation of magnetic particles 113 attached to the examination object 114, and the inductance of the inductors 111 and 121 is affected by that change in permeability. Accordingly, the oscillation frequencies of signals output by the oscillators 110 and 120 change, and a detector (not illustrated) detects the changes in oscillation frequency of the signals. The changes in oscillation frequency indicate fluctuations in the physical properties of the examination object 114.

For example, as illustrated in part of FIG. 10, the examination object 114 is selectively brought into contact with the oscillator 110 in order to use one of the oscillators 110 and 120, namely, the oscillator 110, as a sensor section. The examination object may not be brought into contact with the other oscillator 120 in order to use the oscillator 120 as a reference section, or, as Illustrated in part (b) of FIG. 10, an examination object 124 serving as a reference may be brought into contact with the oscillator 120. Accordingly, the physical properties of the examination object 114 are evaluated by checking the difference in oscillation frequency between the signals of the oscillators 110 and 120 using an enable signal or an /enable signal.

FIG. 11 is a cross-sectional view taken along line A-A' of part of FIG. 10. As illustrated in FIG. 11, even when a metal layer 130 configuring the inductor 111 is formed on the top layer in the semiconductor substrate 101, because there is a protective film 115 formed of an insulator or the like between the surface of the semiconductor substrate 101 and the metal layer 130 (induct of 111), the examination object 114 never contacts the metal layer 130 on the top layer. The same applies to the inductor 121.

In addition, NPL 1 describes a circuit in which, in a sensor IC such as that described above, the oscillation frequency of an oscillator is se to a value within the range from 1.1 GHz to 3.3 GHz in which the fluctuation range of the oscillation frequency in accordance with a change in magnetic susceptibility of magnetic particles is great.

CITATION LIST

Patent Literature

PTL 1: U.S. Patent Application Publication No. 2009/0267596 (Published on Oct. 29, 2009)

Non Patent Literature

NPL 1: C. Sideris, A. HajAmirA, "An Integrated magnetic Spectrometer for Multiplexed Biosensing", IEEE Solid-State Circuit Conf. Dig. Tech. papers, pp. 300-302, February 2013

NPL 2: H. Yada, M. Nagai, K. Tanaka, "Origin of the fast relaxation component of water and heavy water revealed by terahertz time-domain attenuated total reflection spectroscopy", Chemical Physics Letters, pp. 166-170, 2008

SUMMARY OF INVENTION

Technical Problem

However, the above-mentioned sensor IC circuits have a problem that the circuits alone can only perform evaluation using a signal with as a single frequency.

In addition, it is known that, in aqueous solution of electrolyte such as NaCl, ionization of the solute to ions causes a hydration phenomenon in which water molecules are bound to the solute. It is also known that, in aqueous solution of non-electrolyte such as sugar, a hydration phenomenon occurs in which water molecules are bound to the solute through electrostatic force or hydrogen bonding caused by polarity deviation in solute molecules.

As an example, a change in the physical properties of aqueous solution where the solute is protein will be considered. In the aqueous solution, a hydration phenomenon occurs in which water molecules are bound by the activity of the protein. Accordingly, bulk water (water that is sufficiently away from the solute and that is not bound) is reduced, and the permittivity of the bulk water changes to a protein-bound permittivity.

NPL 2 describes the complex permittivity of water. According to NPL 2, the complex permittivity of water greatly fluctuates particularly in the frequency range from 30 GHz to 200 GHz. This fluctuation of the complex permittivity is also considered to be caused by fluctuation of the amount of bulk water.

When the complex permittivity of an examination object fluctuates in the wide frequency range from 30 GHz to 200 GHz, a sensor IC of the related art, such as that described in PTL 1, can only perform evaluation using a signal with a single frequency, and thus cannot detect a difference in the amount of change in the permittivity in accordance with the frequency of a signal. In addition, when a sensor circuit capable of performing evaluation using signals with different frequencies is not nearby, it is impossible to detect, for each frequency, a difference in permittivity change of an examination object whose size is less than or equal to several 100 μm.

In view of the above-described problems, it is an object of the present invention to provide a sensor circuit that can detect changes in the physical properties of an examination object as changes in a plurality of different oscillation frequencies using signals with the oscillation frequencies.

Solution to Problem

To solve the above-described problems, a sensor circuit according to an aspect of the present invention is a sensor circuit including an oscillation circuit whose oscillation frequency changes in accordance with a change in a physical property of an examination object, including: a first oscillation circuit with a first resonant frequency; a second oscillation circuit with a second resonant frequency different from the first resonant frequency; and a detector that detects oscillation frequencies of the first and second oscillation circuits.

Advantageous Effects of Invention

According to the aspect of the present invention, changes in the physical properties of an examination object can be detected as changes in a plurality of different oscillation frequencies using signals with the oscillation frequencies.

DESCRIPTION OF EMBODIMENTS

[First Embodiment]

Figure 1:
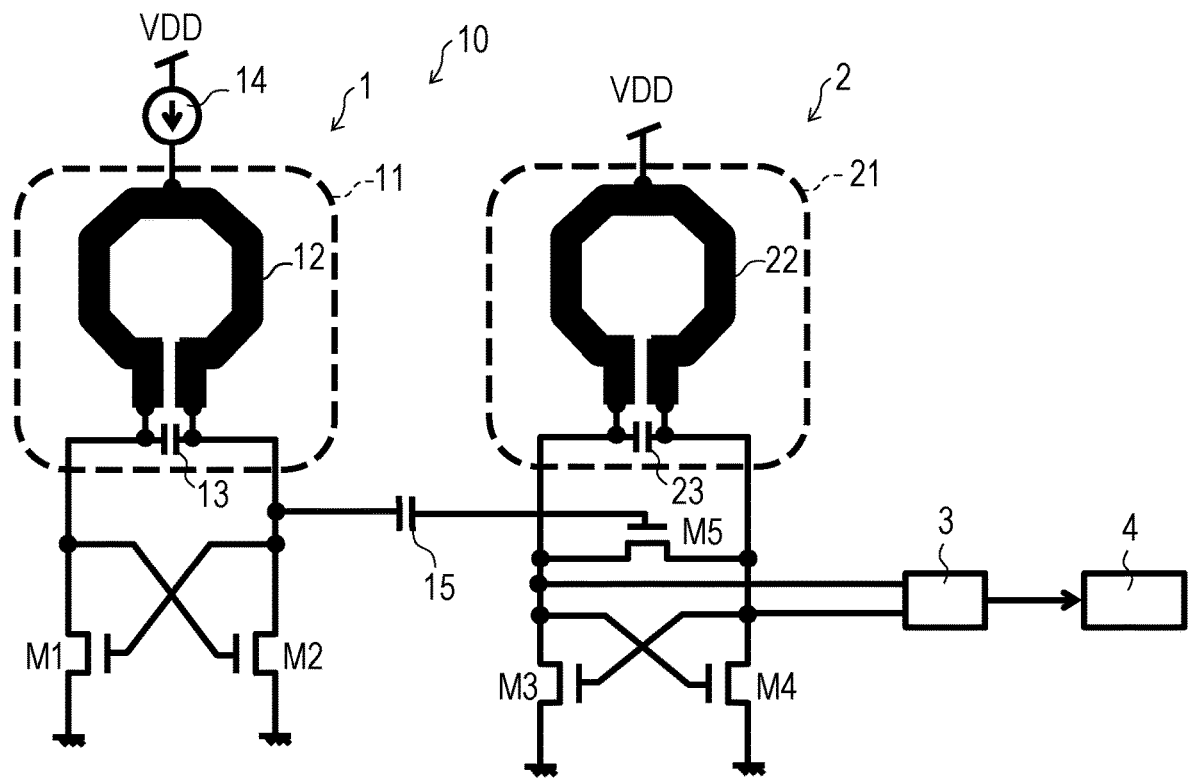
FIG. 1 is a diagram illustrating the configuration of a sensor circuit according to a first embodiment of the present invention.

Hereinafter, a sensor circuit according to the present embodiment will be described on the basis of FIGS. 1 to 7. Note that the configuration described in this embodiment is merely an explanatory example and is not intended to limit the scope of the present invention to that unless otherwise specified. In the drawings described in the following description, portions that have the same functions are given the same reference numeral, and repeated descriptions thereof are omitted.

The sensor circuit according to the present embodiment is a sensor IC (Integrated Circuit) that detects, by bringing an examination object into contact with the surface of a semiconductor substrate, permittivity or permeability of the examination object or permittivity or permeability that changes when the properties of the examination object change.

FIG. 1 is a diagram illustrating the configuration of the sensor circuit according to the present embodiment.

As illustrated in FIG. 1, a sensor circuit 10 includes an oscillation circuit 1 (first oscillation circuit), an oscillation circuit 2 (second oscillation circuit), a frequency-dividing circuit 3, and a detection circuit 4 (detector).

<Oscillation Circuit 1>

The oscillation circuit 1 includes cross-coupled transistors M1 and M2, a resonance circuit 11 formed between the differential outputs of the transistors M1 and M2, and a current source 14 that controls the driving of the oscillation circuit 1 in accordance with a control signal (enable, /enable). The resonance circuit 11 includes an inductor 12 and a capacitor 13 connected in parallel between the differential outputs of the transistors M1 and M2.

The inductor 12 and the capacitor 13 form an LC circuit, and the inductance of the inductor 12 and the capacitance of the capacitor 13 define the resonant frequency (first resonant frequency) of the resonance circuit 11. The inductor 12 and the capacitor 13 are designed such that the resonant frequency of the resonance circuit 11 will be any value within the range from 30 GHz to 200 GHz (inclusive). The range from 30 GHz to 200 GHz (inclusive) is a frequency band in which the complex permittivity particularly of water greatly changes, and changes in the frequency characteristics of permittivity are detectable with high sensitivity.

The oscillation circuit 1 oscillates at an oscillation frequency f1 expressed by the following equation (1) in accordance with the above-mentioned resonant frequency:

$$f1 = 1/\{2\pi\sqrt{(L1 C1)}\} \qquad (1)$$

where L1 is the value of inductance (the number of interlinkage fluxes/current) of the inductor 12, and C1 is the sum of the capacitance (electric capacitance) of the capacitor 13 and parasitic capacitance applied to the inductor 12 when an examination object serving as a reference is mounted.

Because the resonance circuit 11 is not an antenna in a narrow sense that transmits/receives electromagnetic waves, the aperture diameter is not limited by the wavelength. Therefore, the size of the resonance circuit 11 came be less than or equal to a 200-μm square (a size that is accommodated in a square whose each side is 200 μm), which is smaller than the quarter wavelength of about 1.5 mm, which is the wavelength of 200-GHz electromagnetic waves.

The inductor 12 is formed on the outermost layer (a layer that is closest to a position at which semiconductor substrate (substrate) (not illustrated) and an examination object contact each other), among metal layers of the semiconductor substrate. Accordingly, the examination object can be easily brought closer to a portion where the inductor 12 is provided, and changes in the physical properties of the examination object can be more accurately detected. The inductor 12 occupies a large portion of the circuit size of the resonance circuit 11.

In the present embodiment, the area of the inductor 12 is defined such that the size of the resonance circuit 11 in plan view will be a size that is accommodated in a square whose each side is 200 μm. Note that the capacitor 13 may be formed of the gate capacitance of the transistors M1 and M2, or the parasitic capacitance of a wire (not illustrated).

<Oscillation Circuit 2>

Like the oscillation circuit 1, the oscillation circuit 2 includes cross-coupled transistors M3 and M4, and a resonance circuit 21 formed between the differential outputs of he transistors M.3 and M4. The resonance circuit 21 includes an inductor 22 and a capacitor 23 connected in parallel between the differential outputs of the transistors M3 and M4, and a switch transistor M5 connected between the differential outputs of the transistors M3 and M4. The gate of the switch transistor M5 is connected to the drain of the transistor M2 of the oscillation circuit 1 via a capacitor 15.

The inductor 22 and the capacitor 23 form an LC circuit, and the inductance of the inductor 22 and the capacitance of the capacitor 23 define the resonant frequency (second resonant frequency) of the resonance circuit she inductor 22 and the capacitor 23 are designed such that the resonant frequency of the resonance circuit 21 will be a value that is within the range from 30 GHz to 200 GHz (inclusive), and that is about 1/N (N is an arbitrary number greater than 1) of the resonant frequency of the resonance circuit 11.

The oscillation circuit 2 oscillates at an oscillation frequency f2 expressed by the following equation (2) in accordance with the above-described resonant frequency:

$$f2=1/\{2\pi\sqrt{(L2C2)}\} \quad (2)$$

where L2 is the value of inductance of the inductor 22, and C2 is the sum of the capacitance of the capacitor 23 and parasitic capacitance applied to the inductance 22 when an examination object serving as a reference is mounted.

<Frequency-Dividing Circuit 3 and Detection Circuit 4>

The frequency-dividing circuit 3 is connected to the drains of the transistors M3 and M4 of the oscillation circuit 2, and is a frequency divider that divides the frequency of an output signal of the oscillation circuit 2 and outputs the frequency-divided signal to the detection circuit 4 It is assumed that the division ratio of the frequency-dividing circuit 3 is 1/X (X is an arbitrary number greater than 1). Accordingly, the frequency of a signal input to the detection circuit 4 is accommodated in a frequency band in which the detection circuit 4 operates. Note that the frequency-dividing circuit 3 is not an essential configuration for solving the problems of the present invention.

The detection circuit 4 detects the oscillation frequency of the oscillation circuit 1 or the oscillation circuit 2 on the basis of an output signal output by the frequency-dividing circuit 3. That is, the detection circuit 4 counts a signal input in a certain time (such as 10 msec) by referring to the output signal of the frequency-dividing circuit 3, and detects (estimates) the oscillation frequency of the oscillation circuit 1 or the oscillation circuit 2 on the basis of the division ratio of the frequency-dividing circuit 3 and 1 sec/certain time. Note that the detection circuit 4 includes a counter circuit that counts a change in the frequency of a signal output from the frequency-dividing circuit 3 for a certain time.

<Operation of Sensor Circuit>

The sensor circuit 10 is capable of switching between two operating states in accordance with a control signal (enable, /enable) input to the current source 14 of the oscillation circuit 1. Hereinafter, the operating state of the sensor circuit 10 will be described.

(First Operating State)

The sensor circuit 10 operates in a first operating state when the control signal input to the current source 14 enters a conducting state (enable). In the first operating state, the oscillation circuit outputs an oscillation signal from the drain terminals of the transistors M1 and M2 as a differential signal, and the oscillation circuit 2 operates as a frequency-dividing circuit that divides the frequency of the output of the oscillation circuit 1.

It is assumed that a signal output from the drain terminal of the transistor M2 is output via the capacitor 15 to the switch transistor M5 of the oscillation circuit 2 operating as a frequency-dividing circuit (a circuit that applies a bias voltage is not illustrated).

Because the switch transistor M5 is connected between the differential outputs of the cross-coupled transistors M3 and MA, the oscillation circuit 2 operates as an injection-locked frequency-dividing circuit. That is, using the output signal of the oscillation circuit 1 as a sync signal, the oscillation circuit 2 outputs, to the frequency-dividing circuit 3, an output signal that is in sync with a frequency of 1/N of the oscillation circuit 1 and that has a frequency of 1/N of the output frequency (f1) of the oscillation circuit 1.

Figure 2:
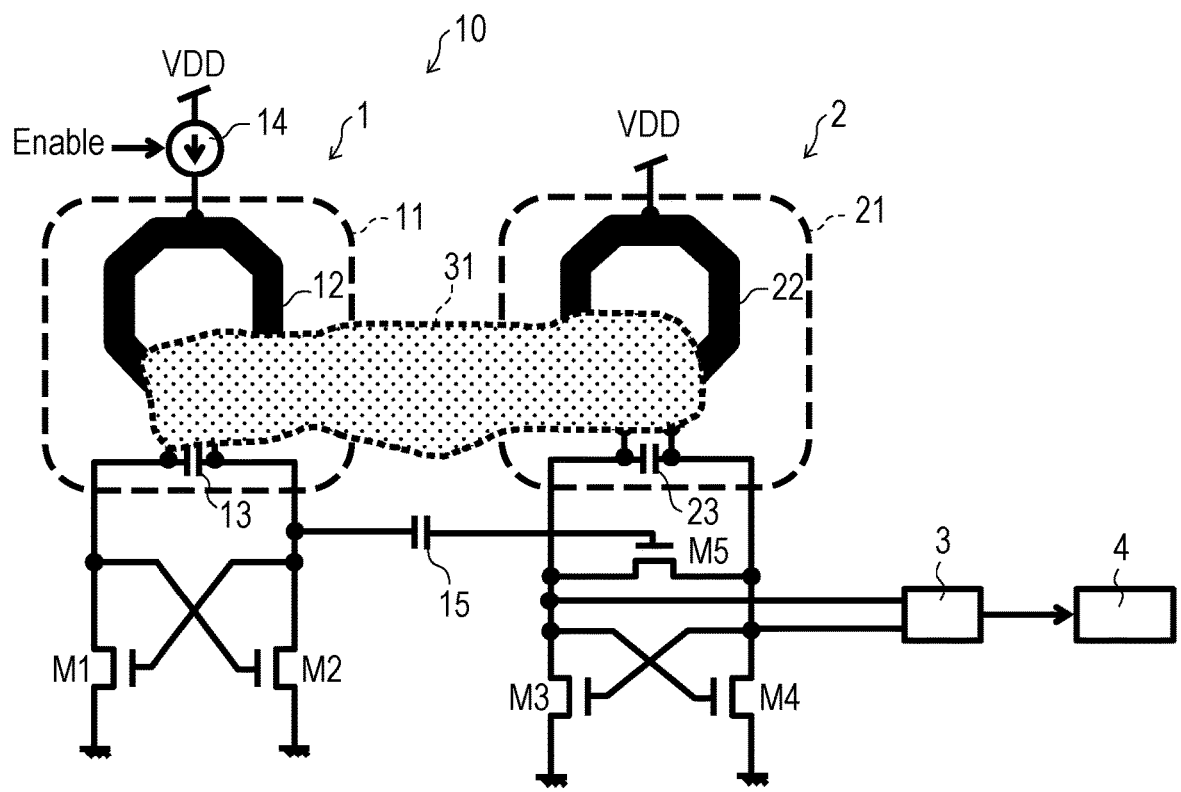
FIG. 2 is a schematic diagram illustrating a state in which an examination object is brought into contact with the sensor circuit in a first operating state.

FIG. 2 is a schematic diagram illustrating a state in which an examination object is brought into contact with the sensor circuit in the first operating state.

Figure 3:
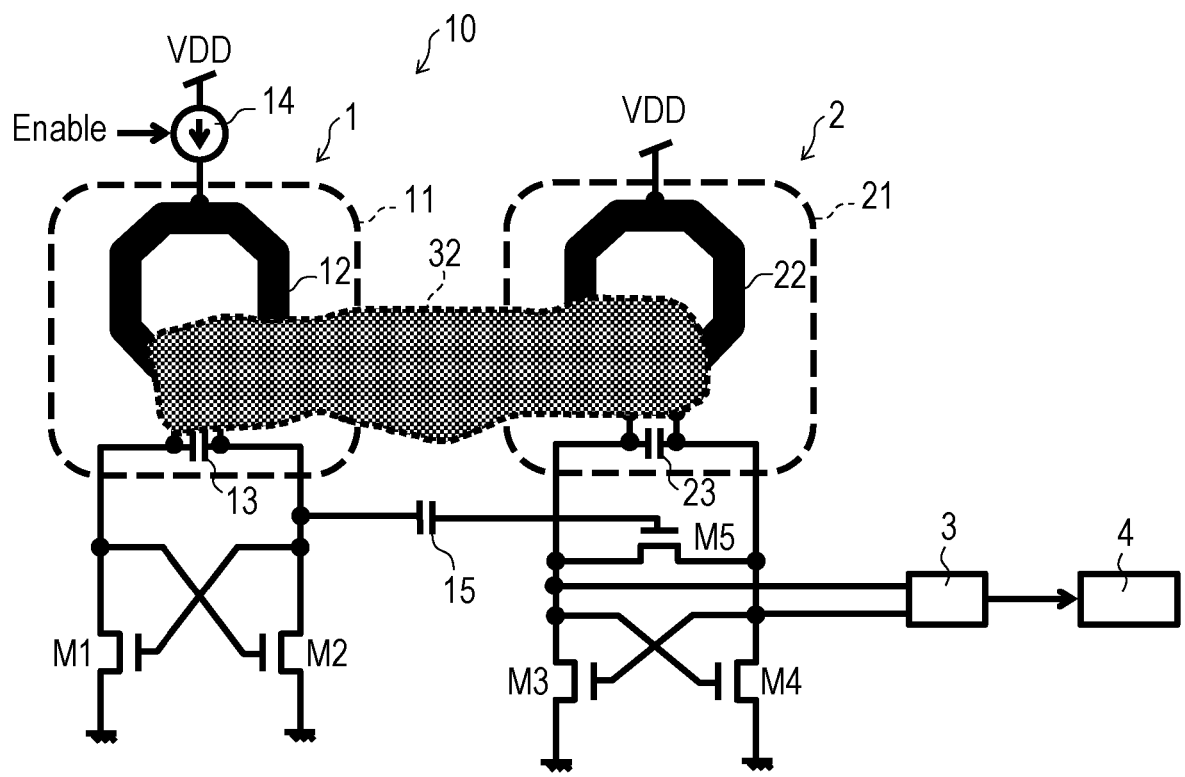
FIG. 3 is a schematic diagram illustrating a state in which the properties of the examination object are changed.

FIG. 3 is a schematic diagram illustrating a state in which the properties of the examination object are changed.

Figure 4:
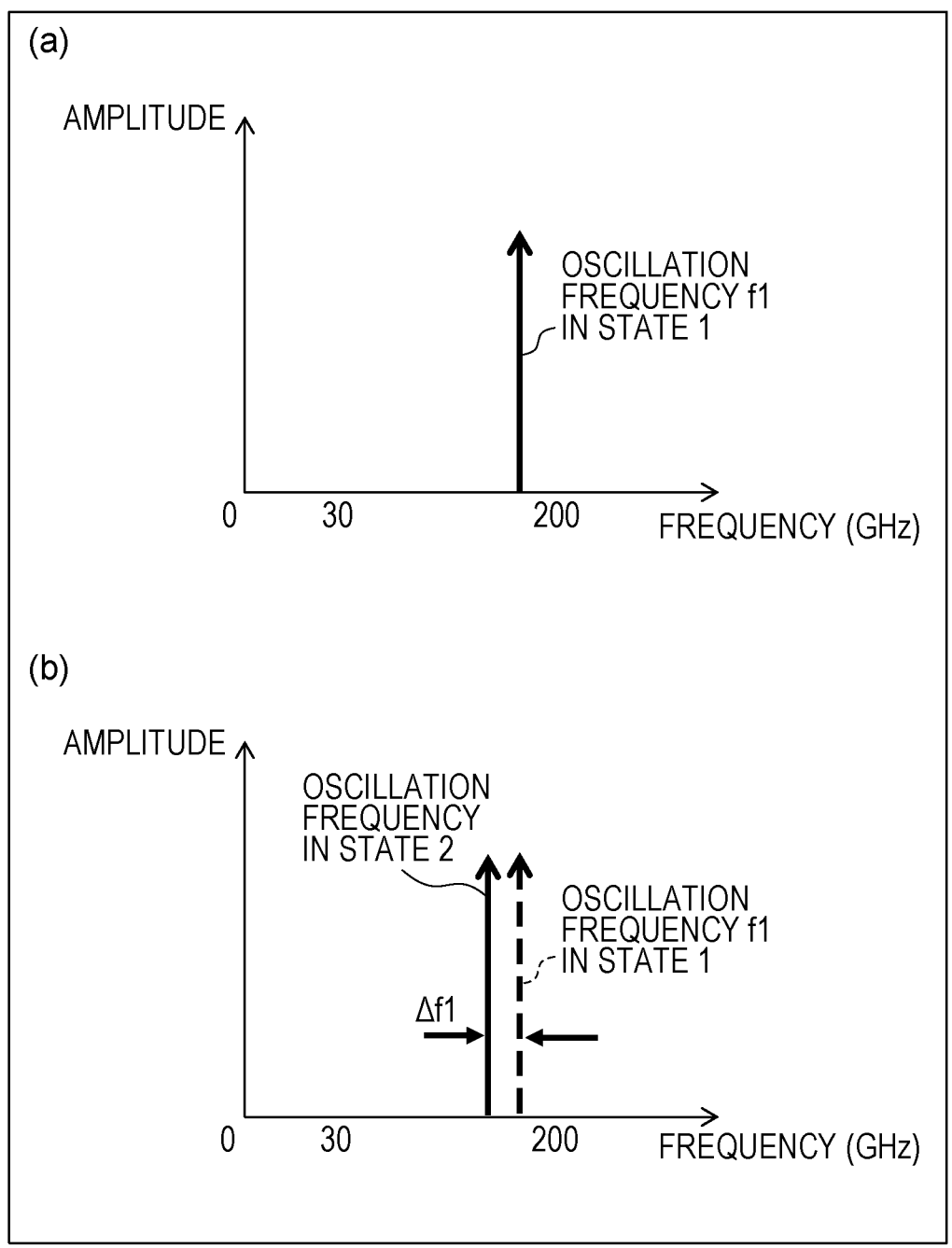
FIG. 4 art (a) is a graph illustrating the oscillation frequency of an oscillation circuit in a state Illustrated in FIG. 2, and part (b) is a graph illustrating the oscillation frequency of the oscillation circuit in a state illustrated in FIG. 3.

Part (a) of FIG. 4 is a graph illustrating the oscillation frequency of the oscillation circuit in a state illustrated in FIG. 2, and part (b) of FIG. 4 is a graph illustrating the oscillation frequency of the oscillation circuit in a state illustrated in FIG. 3. It is assumed that examination objects 31 and 32 include moisture.

As illustrated in FIG. 2, the user brings the examination object 31 before its properties (physical properties) change (first state) into contact with the vicinity of an area where the inductor 12 is formed. Next, using the current source 14, the user causes the oscillation circuit 1 to start operating.

Accordingly, the oscillation circuit 1 oscillates at an oscillation frequency in the first state, illustrated in part (a) of FIG. 4. The oscillation frequency of the oscillation circuit 1 is divided by the oscillation circuit 2 and the frequency-dividing circuit 3 to a frequency of 1/(N·X) and is counted by the detection circuit 4 for a certain time. The detection circuit 4 estimates that the oscillation frequency of the oscillation circuit 1 is a frequency in the first state, illustrated in part (a) of FIG. 4, and holds that frequency value as a reference frequency.

After that, the properties of the examination object 31 change, and, as illustrated in FIG. 3, become the properties of the examination object 32 (second state). As a result, the permittivity of water included in the examination object 31 changes to the permittivity of water included in the examination object 32. In the second state, the user causes the current source 14 to output an enable signal to the oscillation circuit 1. Accordingly, the oscillation circuit 1 starts oscillating, and, as illustrated in part (b) of FIG. 4, oscillates at as oscillation frequency in the second state.

As in the first state, the oscillation frequency of the oscillation circuit 1 in the second state is also divided by the oscillation circuit 2 and the frequency-dividing circuit 3 to a frequency of 1/(N·X) and is counted by the detection circuit 4 for a certain time. Furthermore, the detection circuit 4 estimates that the frequency of the oscillation circuit 1 is a frequency in the second state, illustrated in part (b) of FIG. 4.

As the properties of the examination object change from the examination object 31 to the examination object 32, the permittivity of water included in the examination object changes. Next, when the permittivity (ε) changes, out of the capacitance C1, a parasitic capacitance component applied to the inductor 12 of the oscillation circuit 1 chances. This is clear from the equation C=ε×d/S (d: thickness of dielectric, and S: area of dielectric). A difference ΔC1, before and after the changes in the properties, in the capacitance value C1 of the entirety corresponding to the sum of the capacitance of the capacitor 13 and the parasitic capacitance value is expressed as a difference Δf1 in the oscillation frequency of the oscillation circuit 1. The relational equation between the difference Δf1 and the difference ΔC1 is indicated as the following equation (3):

$$\Delta f1 = 1/[2\pi\sqrt{\{L1(C1+\Delta C1)\}}] - 1/\{2\pi\sqrt{(L1C1)}\} \quad (3)$$

In this manner, the sensor circuit 10 can evaluate changes in the physical properties of the examination object using a signal with the oscillation frequency of the oscillation circuit 1 in the first operating state.

(Second Operating State)

The oscillation circuit 1 does not operate when the control signal input to the current source 14 enters a non-conducting state (enable). In the second operating state, the oscillation circuit 1 does not output an oscillation signal, and the oscillation circuit 2 operates as a normal oscillation circuit.

By grounding a bias voltage applied to the transistor M5 (voltage 0 V), the switch transistor M5 is turned off. Although the switch transistor M5 is connected between the differential outputs of the cross-coupled transistors M3 and M4, because the switch transistor M5 is off, the oscillation circuit 2 can operate as an oscillation circuit.

That is, the oscillation circuit 2 operates as an oscillation circuit that performs a free-run operation at a frequency of about 1/N of the oscillation circuit 1, and a signal output at that oscillation frequency (f2) is input to the frequency-dividing circuit 3. The frequency-dividing circuit 3 is a frequency divider that outputs the output signal of the oscillation circuit 2 to the detection circuit 4. The division ratio of the frequency-dividing circuit 3 is 1/X.

Figure 5:
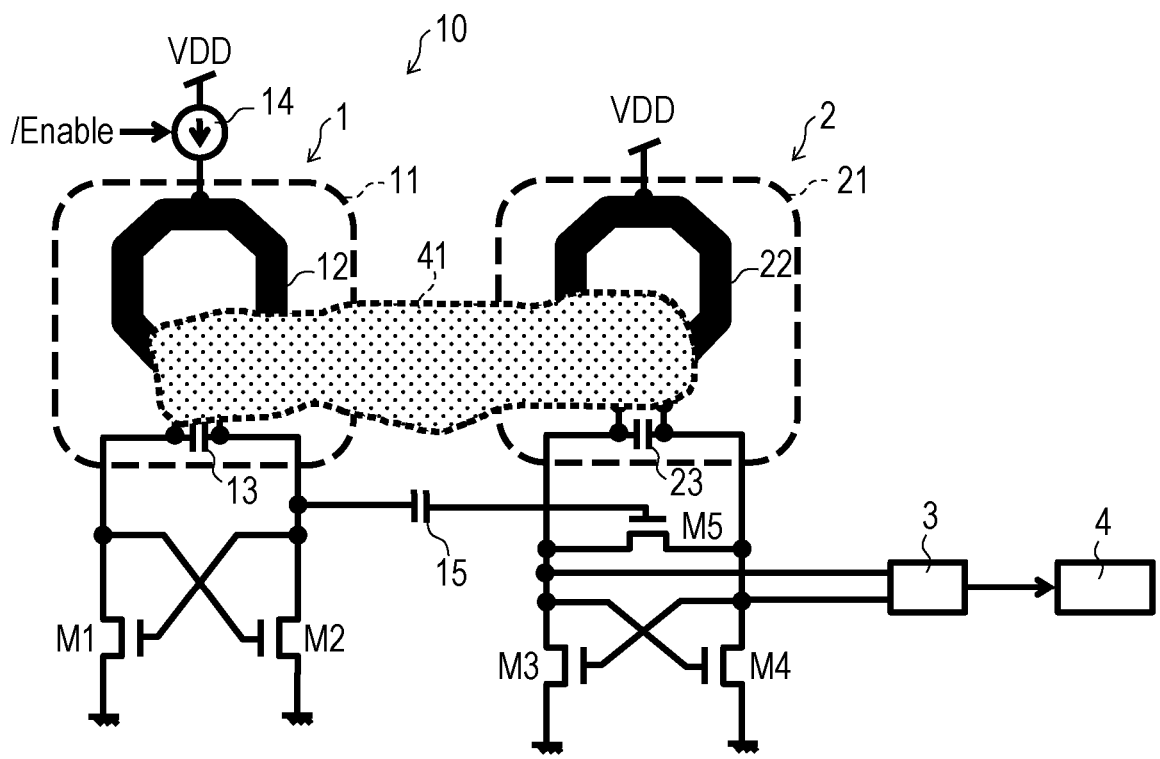
FIG. 5 is a schematic diagram illustrating a state in which an examination object is brought into contact with the sensor circuit in a second operating state.

FIG. 5 is a schematic diagram illustrating a state in which an examination object is brought into contact with the sensor circuit in the second operating state.

Figure 6:
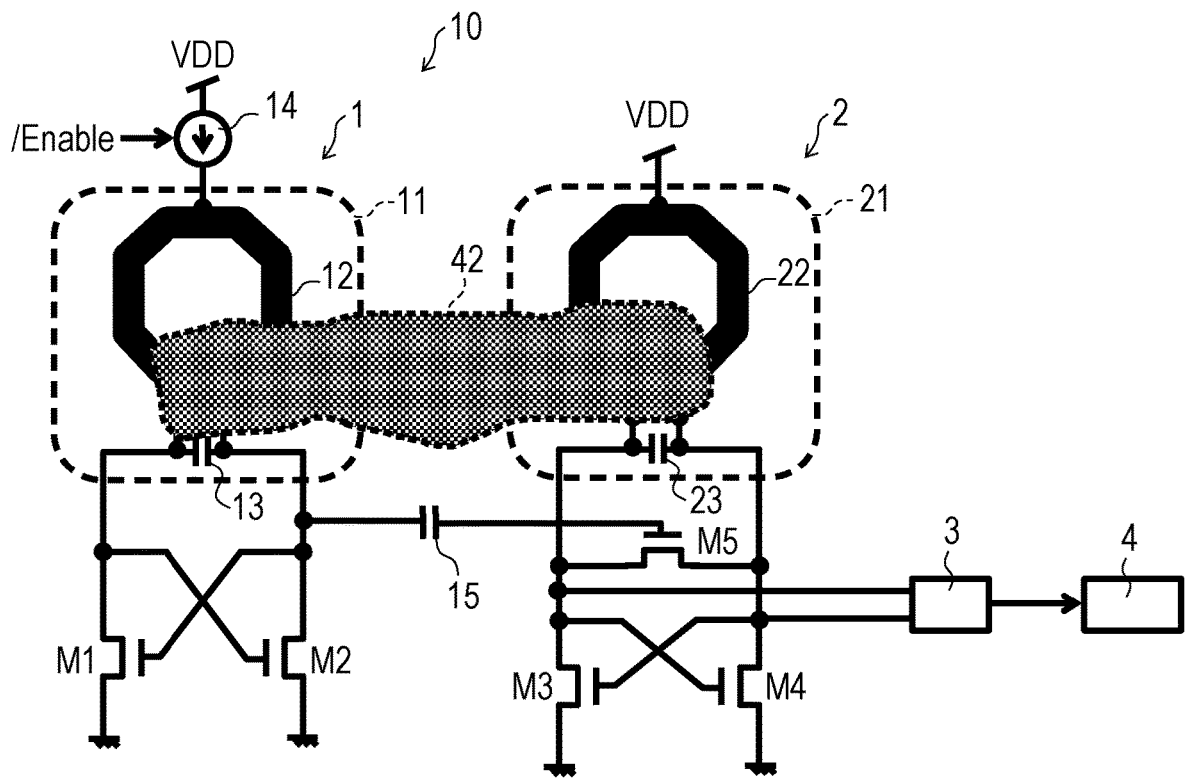
FIG. 6 is a schematic diagram illustrating a state in which the properties of the examination object are changed.

FIG. 6 is a schematic diagram illustrating a state in which the properties of the examination object are changed.

Figure 7:
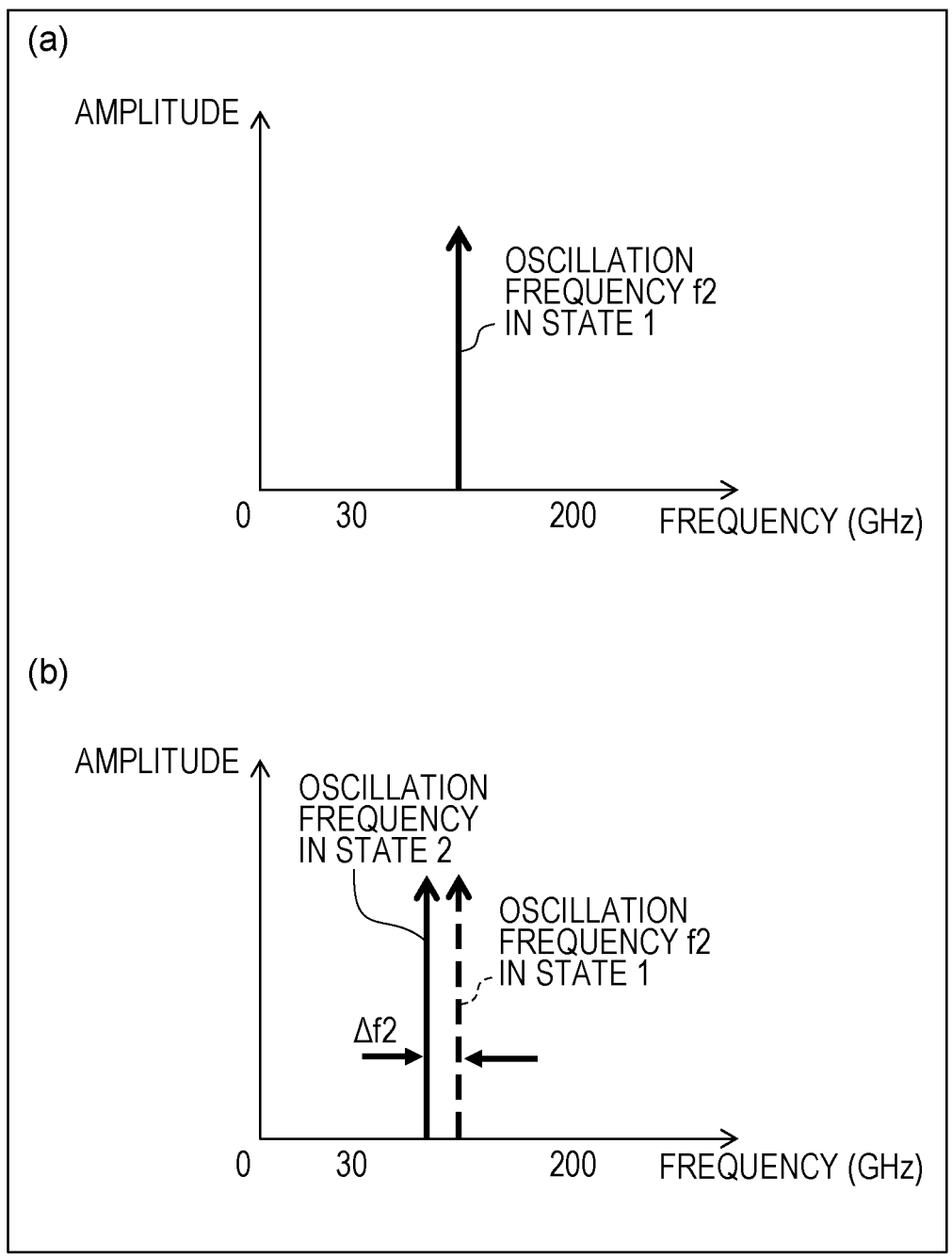
FIG. 7 Part (a) is a graph illustrating the oscillation frequency of the oscillation circuit in a state illustrated in FIG. 5, and part (b) is a graph illustrating the oscillation frequency of the oscillation circuit in a state illustrated in FIG. 6.

Part (a) of FIG. 7 is a graph illustrating the oscillation frequency of the oscillation circuit in a state illustrated in FIG. 5, and part (b) of FIG. 7 is a graph illustrating the oscillation frequency of the oscillation circuit in a state illustrated in FIG. 6.

As illustrated in FIG. 5, the user brings an examination object 41 before its properties (physical properties) change (first state) into contact with the vicinity of an area where the inductor 22 is formed. Next, the user causes the oscillation circuit 2 to start operating.

Accordingly, the oscillation circuit 2 oscillates at an oscillation frequency in the first state, illustrated in part of FIG. 7. The oscillation frequency of the oscillation circuit 2 is divided by the frequency-dividing circuit 3 to a frequency of 1/X and is counted by the detection circuit 4 for a certain time. The detection circuit 4 estimates that the oscillation frequency of the oscillation circuit 2 is a frequency in the first state, illustrated in part (a) of FIG. 7, and holds that frequency value as a reference frequency.

After that, the properties of the examination object 41 change, and, as illustrated in FIG. 6, become the properties of an examination object 42 (second state). As a result, the permittivity of water included in the examination object 41 changes to the permittivity of water included in the examination object 42. Because no enable signal is input to the oscillation circuit 1, the oscillation circuit 1 is in an off state and is stopped. Therefore, the gate voltage of the switch transistor M5, which serves as an output signal of the oscillation circuit 1, is 0 V; and the oscillation circuit 2 operates as an oscillator, and, as illustrated in part (b) of FIG. 7, oscillates at an oscillation frequency in the second state.

As in the first state, the oscillation frequency of the oscillation circuit 2 in the second state is also divided by the frequency-dividing circuit 3 so a frequency of 1/X and is counted by the detection circuit 4 for a certain time. Furthermore, the detection circuit 4 estimates that the frequency of the oscillation circuit 2 is a frequency in the second state, illustrated in part (b) of FIG. 7.

As the properties of the examination object chance from the examination object 41 to the examination object 42, the permittivity of water included in the examination object changes. Next, when the permittivity (ε) changes, out of the capacitance C2, a parasitic capacitance component as to the inductor 22 of the oscillation circuit. 2 changes. A difference ΔC2, before and after the changes in the properties, in the capacitance value C2 of the entirety corresponding to the sum of the capacitance of the capacitor 23 and the parasitic capacitance value is expressed as a difference Δf2 in the oscillation frequency of the circuit 2. The relational equation between the difference Δf2 and the difference ΔC2 is indicated as the following equation (4):

$$\Delta f2 = 1/[2\pi\sqrt{\{L2(C2+\Delta C2)\}}] - 1/\{2\pi\sqrt{(L2C2)}\} \quad (4)$$

In this manner, the sensor circuit 10 can evaluate changes in the physical properties of the examination object using a signal with the oscillation frequency of the oscillation circuit 2 in the second operating state.

By switching between the first operating state and the second operating state in accordance with the control signal, the sensor circuit 10 can detect changes in the physical properties of an examination object as changes in a plurality of different oscillation frequencies using signals with the oscillation frequencies.

[Second Embodiment]

Another embodiment of the present invention will be described as follows on the basis of FIG. 8. For convenience of explanation, members having the same functions as the members described in the above embodiment are given the same reference numerals, and descriptions thereof are omitted.

Figure 8:
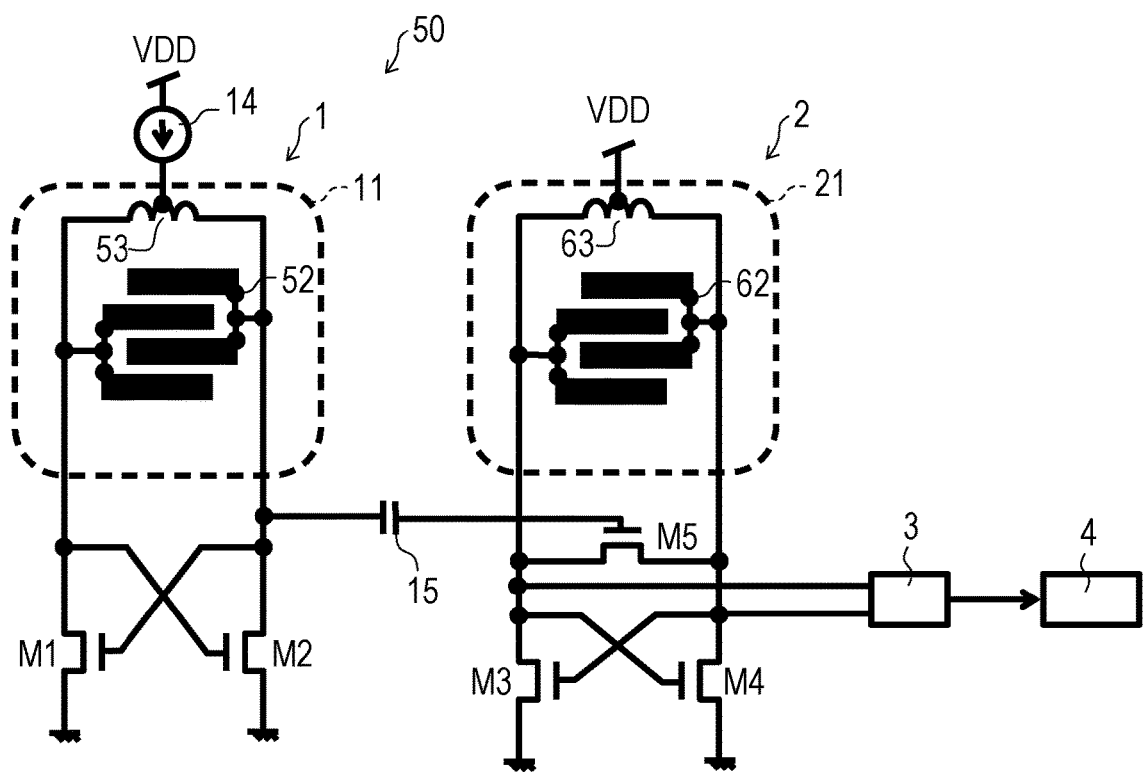
FIG. 8 is a diagram illustrating the configuration of a sensor circuit according to a second embodiment of the present invention.
Figure 9:
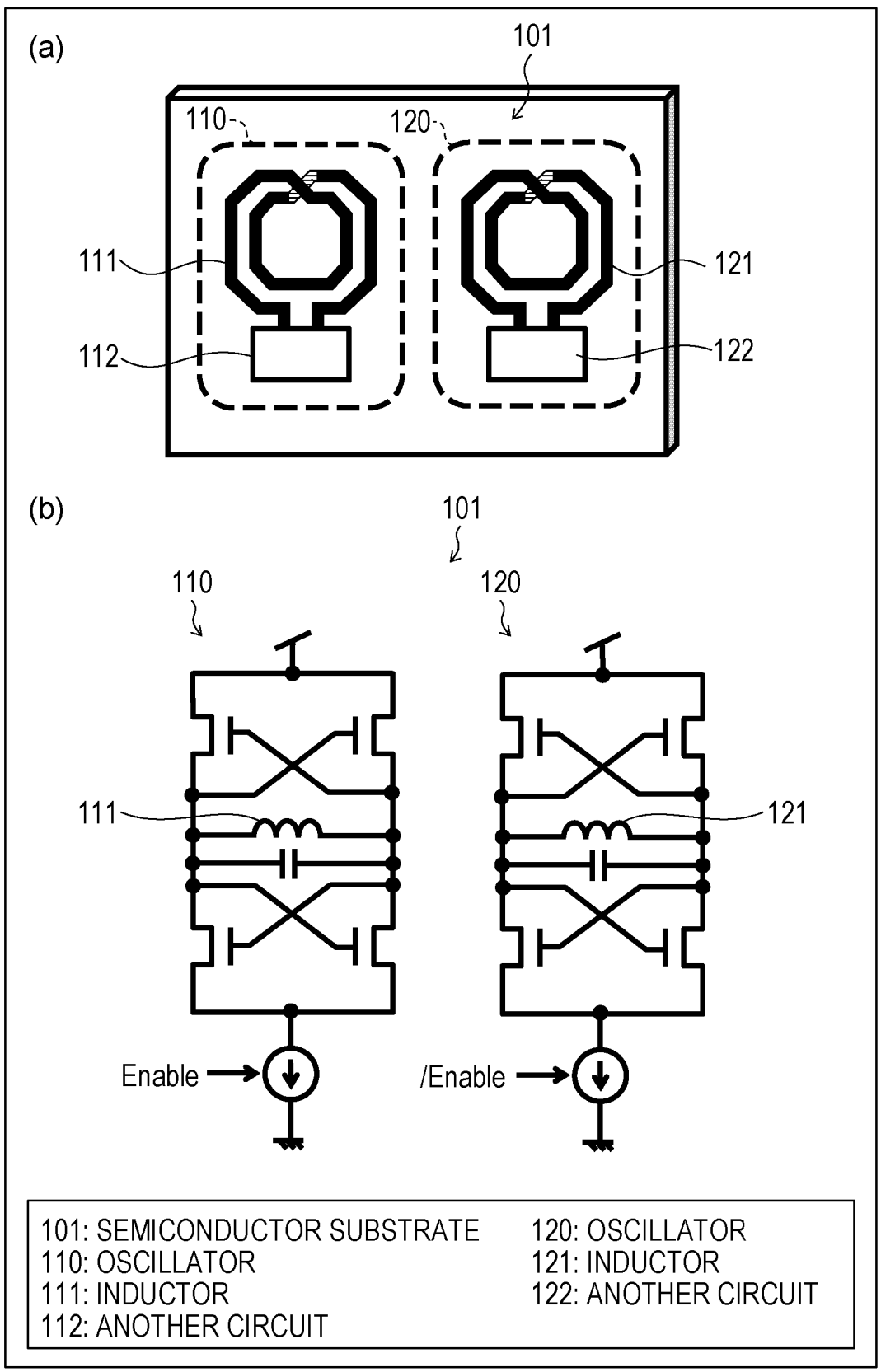
FIG. 9 Part (a) is a schematic diagram illustrating the configuration of a sensor IC of PTL 1, and part (b) is a circuit diagram of the sensor IC of PTL 1.
Figure 10:
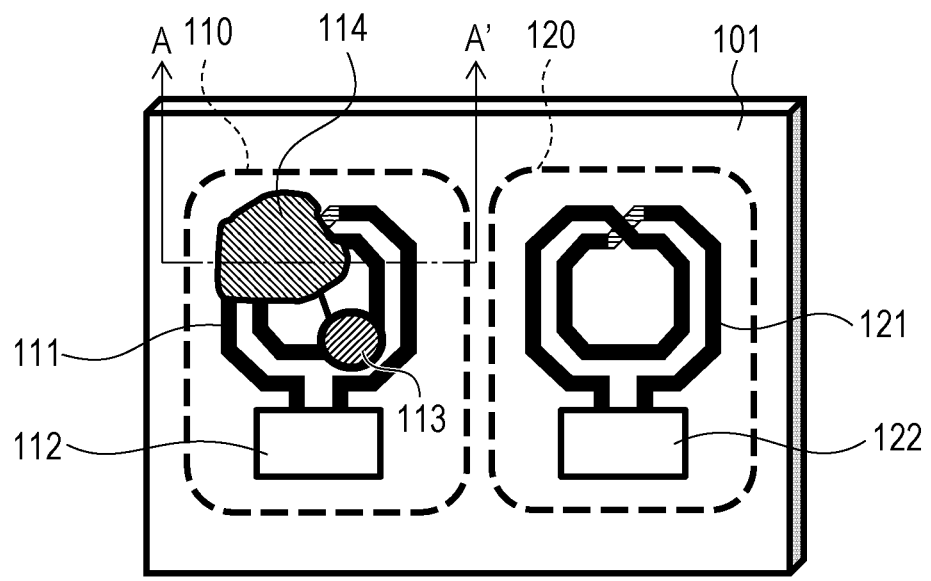
FIG. 10 Part (a) is a schematic diagram illustrating a state in which magnetic particles and an examination object are brought into contact with one of two inductors of the sensor IC, and part (b) is a diagram illustrating a state in which a further examination object is brought into contact with the other conductor.
Figure 10:
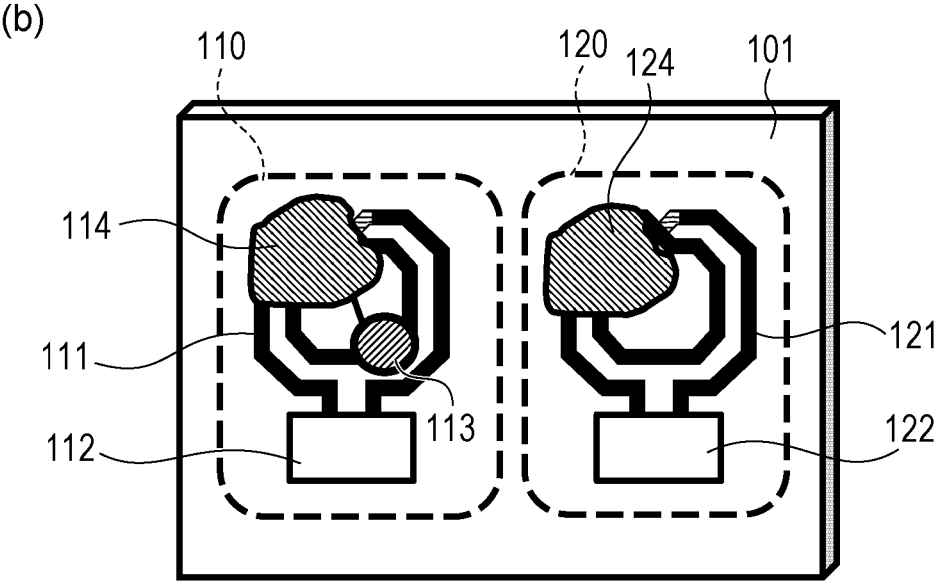
Figure 11:
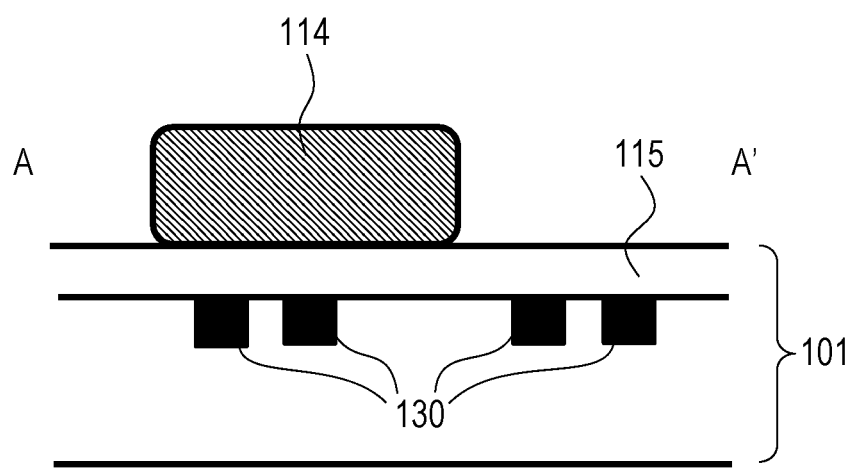
FIG. 11 is a cross-sectional view taken along line A-A' of part (a) of FIG. 10.

FIG. 8 is a diagram illustrating the configuration of a sensor circuit according to the present embodiment.

As illustrated in FIG. 8, the oscillation circuit 1 of a sensor circuit 50 includes the resonance circuit 11 formed between the differential outputs of the drain terminals of the transistors M1 and M2, and the current source 14, which controls the driving of the oscillation circuit 1 in accordance with a control signal. The oscillation circuit 1 has a resonant frequency with any value within the range from 30 GHz to 200 GHz (inclusive).

The oscillation circuit 2 includes the resonance circuit 21 formed between the differential outputs of the drain terminals of the transistors M3 and M4. The oscillation circuit 2 has a resonant frequency that is within the range from 30 GHz to 200 GHz (inclusive) and that has a value of about 1/N (N is an arbitrary number greater than 1) of the resonant frequency of the oscillation circuit 1.

Compared with the sensor circuit 10 of the first embodiment, the sensor circuit 50 of the present embodiment is different in the configuration of inductors 53 and 63 and capacitors 52 and 62 in the resonance circuits 11 and 21.

As illustrated in FIG. 8, in the sensor circuit 50, the capacitors 52 and 62 are formed on a metal layer that is the top layer among metal layers of the semiconductor substrate. In plan view, the capacitors 52 and 62 are a large portion of an area that the oscillation circuit 1 and the oscillation circuit 2 occupy in the semiconductor substrate, and are comb-shaped capacitors formed of comb-shaped electrodes. Because each inductor formed of a metal layer is circular, the oscillation frequencies of oscillation circuits 11 and 21 vary in accordance with the position of an examination object with respect to the inductor. In contrast, by having the capacitors 52 and 62 as comb shaped capacitors, variations of the oscillation frequencies of the oscillation circuits 11 and 21 in accordance with the position of an examination object with respect to the capacitors 52 and 62 can be suppressed. As a result, changes in the physical properties of an examination object can be more accurately detected.

The inductors 53 and 63 may be formed on a metal layer that is not the top layer, and may be active inductors, for example, formed of transistors.

Like the sensor circuit 10, by switching between the first operating state and the second operating state in accordance with the control signal input to the current source 14 of the oscillation circuit 1, the sensor circuit 50 of the preset embodiment can detect changes in the physical properties of an examination object as changes in a plurality of different oscillation frequencies using signals with the oscillation frequencies.

[Third Embodiment]

Another embodiment of the present invention will be described as follows. For convenience of explanation, members having the same functions as the members described in the above embodiments are given the same reference numerals, and descriptions thereof are omitted.

In a sensor circuit of the present embodiment, the resonant frequency of the resonance circuit 21 is different from the resonant frequency of the resonance circuit 21 in the sensor circuit 10 of the above-described first embodiment and the sensor circuit 50 of the second embodiment.

That is, it has been described that, in the sensor circuit 10 of the above-described first embodiment and the sensor circuit 50 of the second embodiment, the resonant frequency of the resonance circuit 21 is designed to be a value that is within the range from 30 GHz to 200 GHz (inclusive) and that is about 1/N (N is an arbitrary number greater than 1) of the resonant frequency of the resonance circuit 11. In contrast, in the sensor circuit of the present embodiment, the resonant frequency of the resonance circuit 21 is designed to be a value that is within the range from 30 GHz to 200 GH (inclusive) and that is about 1/N (N is an arbitrary number less than 1) of the resonant frequency of the resonance circuit 11.

In other words, in the sensor circuit of the present embodiment, the resonant frequency of the resonance circuit 21 may be greater than the resonant frequency of the resonance circuit 11 in some cases. As a result, the oscillation frequency of the oscillation circuit 2 is greater than the oscillation frequency of the oscillation circuit 1, and, in the first operating state, the oscillation circuit 2 operates as a frequency-multiplying circuit.

Like the sensor circuit of the present embodiment, even when the oscillation frequency of the oscillation circuit 2 is greater than the oscillation frequency of the oscillation circuit 1, changes in the physical properties of an examination object can be detected as changes in a plurality of different oscillation frequencies using signals with the oscillation frequencies.

[Fourth Embodiment]

Another embodiment of the present invention will be described as follows. For convenience of explanation, members having the same functions as the members described in the above embodiments are given the same reference numerals, and descriptions thereof are omitted.

Although the sensor circuits of the above-described first to third embodiments have been described such that the oscillation circuit 2 operates as a frequency-dividing (multiplying) circuit in the first operating state and the oscillation circuit 2 operates as a normal oscillation circuit in the second operating state by switching between the first operating state and the second operating state, the present invention is not limited to these cases.

That a frequency-dividing circuit 3A and a detection circuit 4A corresponding to the oscillation circuit 1 and a frequency-dividing circuit 3B and a detection circuit 4B corresponding to the oscillation circuit 2 may be separately provided; and the oscillation frequency of the oscillation circuit I may be detected by the frequency-dividing circuit 3A and the detection circuit 4A, and the oscillation frequency of the oscillation circuit 2 may be detected by the frequency-dividing circuit 3B and the detection circuit 4B.

Like the sensor circuit of the present embodiment, even when the frequency-dividing circuit 3A and the detection circuit 4A corresponding to the oscillation circuit 1 and the frequency-dividing circuit 3B and the detection circuit 4B corresponding to the oscillation circuit 2 are separately provided, changes in the physical properties of an examination object can be detected as changes in a plurality of different oscillation frequencies using signals with the oscillation frequencies.

CONCLUSION

A sensor circuit according to a first aspect of the present invention is a sensor circuit (10, 50) including an oscillation circuit whose oscillation frequency changes in accordance with changes in the physical properties of an examination object (31, 32, 41, 42), including: a first oscillation circuit (oscillation circuit 1) with a first resonant frequency; a second oscillation circuit (oscillation circuit 2) with a second resonant frequency different from the first resonant frequency; and a detector (detection circuit 4) that detects the oscillation frequencies of the first and second oscillation circuits.

According to the above-described configuration, the first oscillation circuit and the second oscillation circuit oscillate at different resonant frequencies in accordance with their resonant frequencies, and the detection circuit detects the oscillation frequencies of the first oscillation circuit and the second oscillation circuit.

Accordingly, changes in the physical properties of an examination object can be detected as changes in a plurality of different oscillation frequencies for each of the oscillation frequencies using signals with the oscillation frequencies.

The sensor circuit according to a second aspect of the present invention may be, in the first aspect, capable of switching, in accordance with a control signal input to the first oscillation circuit, between a first operating state in which the first oscillation circuit operates and the second oscillation circuit divides or multiplies the frequency of a signal with the oscillation frequency of the first oscillation circuit and outputs the frequency-divided or -multiplied signal, and a second operating state in which the first oscillation circuit stops and the second oscillation circuit oscillates at an oscillation frequency based on the second resonant frequency.

According to the above-described configuration, changes in the physical properties of an examination object can be detected as changes in a plurality of different oscillation frequencies output from similar circuits for each of the oscillation frequencies using signals with the oscillation frequencies.

In the sensor circuit according to a third aspect of the present invention, in the second aspect, in the first operating state, in response to an input of an output signal of the first oscillation circuit as a sync signal to the second oscillation circuit, the second oscillation circuit may operate as a frequency-dividing circuit that divides the frequency of a signal with the oscillation frequency of the first oscillation circuit and output the frequency-divided signal.

According to the above-described configuration, the design of the second oscillation circuit can be an efficient design.

In the sensor circuit according to a fourth aspect of the present invention, in any of the first to third aspects, the first oscillation circuit and the second oscillation circuit may each include a substrate and an inductor (12, 22), and the inductor may be formed on an outermost layer of the substrate.

According to the above-described configuration, the examination object can be easily brought close to a portion where the inductors of the sensor circuit are provided, and changes in the physical properties of the examination object can be more accurately detected.

In the sensor circuit according to a fifth aspect of the present invention, in any of the first to fourth aspects, the first oscillation circuit and the second oscillation circuit may each include a capacitor (52, 62), and the capacitor may include a comb-shaped electrode.

According to the above-described configuration, by having the capacitors as comb-shaped capacitors, variations of the oscillation frequencies of the first oscillation circuits and the second oscillation circuit in accordance with the position of an examination object with respect to the comb-shaped capacitors can be suppressed. As a result, changes in the physical properties of the examination object can be more accurately detected.

The present invention is not limited to each of the above-described embodiments, and various changes are possible within a scope defined by the claims. An embodiment achieved by appropriately combining technical means disclosed in different embodiments is also included in the technical scope of the present invention. Furthermore, a new technical feature can be formed by combining technical means disclosed in each of the embodiments.

REFERENCE SIGNS LIST

1: oscillation circuit (first oscillation circuit)
2: oscillation circuit (second oscillation circuit)
4: detection circuit (detector)
10, 50: sensor circuit
12, 22, 53, 63: inductor
13, 23, 52, 62: capacitor
31, 32, 41, 42: examination object

The invention claimed is:

1. A sensor circuit including an oscillation circuit whose oscillation frequency changes in accordance with a change in a physical property of an examination object, comprising:
a first oscillation circuit with a first resonant frequency;
a second oscillation circuit with a second resonant frequency different from the first resonant frequency; and
a detector that detects oscillation frequencies of the first and second oscillation circuits;
wherein the sensor circuit is capable of switching, in accordance with a control signal input to the first oscillation circuit, between
a first operating state in which the first oscillation circuit operates, and the second oscillation circuit divides or multiplies the frequency of a signal with the oscillation frequency of the first oscillation circuit and outputs the frequency-divided or -multiplied signal, and
a second operating state in which the first oscillation circuit stops, and the second oscillation circuit oscillates at an oscillation frequency based on the second resonant frequency.

2. The sensor circuit according to claim 1, wherein, in the first operating state, in response to an input of an output signal of the first oscillation circuit as a sync signal to the second oscillation circuit, the second oscillation circuit operates as a frequency-dividing circuit that divides the frequency of a signal with the oscillation frequency of the first oscillation circuit and outputs the frequency-divided signal.

3. The sensor circuit according to claim 1, wherein:
the first oscillation circuit and the second oscillation circuit each include a substrate and an inductor, and
the inductor is formed on an outermost layer of the substrate.

4. The sensor circuit according to claim 1, wherein:
the first oscillation circuit and the second oscillation circuit each include a capacitor, and
the capacitor includes a comb-shaped electrode.

5. A sensor circuit including an oscillation circuit whose oscillation frequency changes in accordance with a change in a physical property of an examination object, comprising:
a first oscillation circuit with a first resonant frequency;
a second oscillation circuit with a second resonant frequency different from the first resonant frequency; and
a detector that detects oscillation frequencies of the first and second oscillation circuits;
wherein the sensor circuit is capable of switching, in accordance with a control signal input to the first oscillation circuit, between
a first operating state in which the first oscillation circuit operates, and the second oscillation circuit divides or multiplies the frequency of a signal with the oscillation frequency of the first oscillation circuit and outputs the frequency-divided or -multiplied signal,
a second operating state in which the first oscillation circuit stops, and the second oscillation circuit oscillates at an oscillation frequency based on the second resonant frequency, and the detection of the oscillation frequency is done in the first operating state and the second operating state before and after the change in the physical property of the examination object.

* * * * *